United States Patent
Acosta et al.

(10) Patent No.: US 10,485,987 B2
(45) Date of Patent: Nov. 26, 2019

(54) METHOD FOR PRODUCING DATA REPRESENTING RADIOTHERAPY TREATMENT CONSTRAINTS, DEVICES AND CORRESPONDING PROGRAM

(71) Applicant: UNIVERSITE DE RENNES 1, Rennes (FR)

(72) Inventors: Oscar Acosta, Rennes (FR); Gael Drean, Rennes (FR); Renaud De Crevoisier, Rennes (FR); Pascal Haigron, Rennes (FR)

(73) Assignee: UNIVERSITE DE RENNES 1, Rennes (FR)

( * ) Notice: Subject to any disclaimer, the term of this patent is extended or adjusted under 35 U.S.C. 154(b) by 478 days.

(21) Appl. No.: 14/785,556

(22) PCT Filed: Apr. 18, 2014

(86) PCT No.: PCT/EP2014/058025
§ 371 (c)(1),
(2) Date: Oct. 19, 2015

(87) PCT Pub. No.: WO2014/170491
PCT Pub. Date: Oct. 23, 2014

(65) Prior Publication Data
US 2016/0082283 A1    Mar. 24, 2016

(30) Foreign Application Priority Data

Apr. 18, 2013 (FR) ..................... 13 53552

(51) Int. Cl.
| | |
|---|---|
| *A61N 5/10* | (2006.01) |
| *G06T 7/11* | (2017.01) |
| *G06T 7/149* | (2017.01) |
| *G06T 7/136* | (2017.01) |

(52) U.S. Cl.
CPC .......... *A61N 5/103* (2013.01); *A61N 5/1031* (2013.01); *G06T 7/11* (2017.01); *G06T 7/136* (2017.01);
(Continued)

(58) Field of Classification Search
CPC ................ A61N 5/103; A61N 5/1031; G06T 2207/20076; G06T 2207/30096; G06T 7/11; G06T 7/136
See application file for complete search history.

(56) References Cited

U.S. PATENT DOCUMENTS

2012/0320055 A1    12/2012    Pekar et al.

FOREIGN PATENT DOCUMENTS

| WO | 2012159671 A1 | 11/2012 | |
|---|---|---|---|
| WO | WO 2013028762 A1 * | 2/2013 | ............. A61B 6/463 |

OTHER PUBLICATIONS

Sharif Qatarneh, "Development of a Whold Body Atlas for Radiation Therapy Planning and Treatment Optimization", 2006.
(Continued)

*Primary Examiner* — Christine H Matthews
(74) *Attorney, Agent, or Firm* — David D. Brush; Westman, Champlin & Koehler, P.A.

(57) ABSTRACT

A method is provided for producing data representing radiotherapy treatment constraints associated with a patient to be treated. The method includes: a phase of mapping at least one current atlas of a set of atlases according to at least one datum representing a patient to be treated, providing a map of probability regions at risk; and a phase of generating at least one datum representing a constraint to be applied to a treatment for the patient according to the probability of regions at risk.

10 Claims, 4 Drawing Sheets

(52) U.S. Cl.
CPC .... *G06T 7/149* (2017.01); *G06T 2207/20076* (2013.01); *G06T 2207/30096* (2013.01)

(56) References Cited

OTHER PUBLICATIONS

International Search Report and Written Opinion dated Jun. 23, 2014 for International Application No. PCT/EP2014/058025, filed Apr. 18, 2014.
French Search Report and Written Opinion dated Jun. 12, 2013 for French Application No. 1353552, file Apr. 18, 2013.
English translation of the International Written Opinion dated Jun. 23, 2014 for International Application No. PCT/EP2014/058025, filed Apr. 18, 2014.
Wen Ning et al: "Evaluation of the Deformation and Corresponding Dosimetric Implications in Prostate Cancer Treatment", Physics in Medicine and Biology, Institute of Physics Publishing, Bristol GB, vol. 57, No. 17, Sep. 7, 2012 (Sep. 7, 2012), pp. 5361-5379, XP002693995.
Rizzo G et al: "Multi-Modal Medical Image integration to Optimize Radiotherapy Planning in Lung Cancer Treatment", Annals of Biomedical Engineering, Pergamon Press, Oxford, GB, vol. 32, No. 10, Jan. 1, 2004 (Jan. 1, 2004), pp. 1399-1407, XP002488929.
Miyabe Yiki et al: "New Algorithm to Simulate Organ Movement and Deformation for Four-Dimensional CT and Fluoroscopy of the Thorax", Medical Physics, AIP, Melville, NY, US, vol. 36, No. 10, Sep. 4, 2009 (Sep. 4, 2009), pp. 4328-4339, XP012129704.
European Action dated Aug. 9, 2018, with Machine translation into English, for corresponding French Application No. 14718969.0.

* cited by examiner

METHOD FOR PRODUCING DATA REPRESENTING RADIOTHERAPY TREATMENT CONSTRAINTS, DEVICES AND CORRESPONDING PROGRAM

CROSS-REFERENCE TO RELATED APPLICATIONS

This Application is a Section 371 National Stage Application of International Application No. PCT/EP2014/058025, filed Apr. 18, 2014, the content of which is incorporated herein by reference in its entirety, and published as WO 2014/170491A1 on Oct. 23, 2014, not in English.

1. FIELD OF THE INVENTION

The invention pertains to the processing of medical imaging data. The invention pertains more particularly to a method for processing medical data with a view to planning one or more actions to be carried out, for example actions for applying radiation to one or more given areas in a radiotherapy operation It may be recalled that radiotherapy is a method for treating cancers that uses radiation to destroy the cancer cells. The irradiation is aimed at destroying tumor cells while sparing peripheral healthy tissue. To enable irradiation, a linear electron accelerator is used. This linear electron accelerator produces an irradiation beam.

2. PRIOR ART

The history of radiotherapy is relatively recent. Radiotherapy is gaining in efficacy in line with the development of technical advances. Thus, by using a scanner, it has become possible to plan and/or schedule 3D radiotherapy treatment. This is a major advance over 2D treatment. Treatment based on the use of a scanner enables radio-oncologists to determine the distribution of the radiation dose more precisely by using computed tomography images of the patient's anatomy. Imaging techniques have enabled the emergence of image-guided radiotherapy (IGRT) enabling improved control over the position of the area to be treated as and when the treatment is made. Innovations in treatment devices such as the emergence of multi-leaf collimators have led to intensity-modulated conformal radiotherapy (IMRT) which enables a more precise adaptation of the irradiation to the shape of the organs to be treated. Tumors can thus be viewed and treated more efficaciously. This improves the prognosis for patients, enhances the preservation of healthy organs and leads to fewer side effects.

However, problems remain. Indeed, although the intensity of the irradiation can now be modulated according to determined areas of treatment, it is still true that certain anatomical regions are more sensitive to irradiation than others. These areas of treatment can be organs but also portions of organs. It has been shown that certain portions of organs that are over-irradiated can be responsible on their own for a substantial part of the side effects encountered during radiotherapy treatment.

Thus, for example, in the treatment of cancer in the higher respiratory and gastrointestinal tracts (or head and throat cancer), it is particularly important not to subject the salivary glands to irradiation. Indeed, it has been shown that the irradiation of these salivary glands causes disastrous and counter-productive side effects such as the occurrence of cancer of the salivary glands themselves. It is therefore necessary to protect these salivary glands. This is also true for cancer of the prostate. It has been shown that over-irradiation of a specific sub-region of the rectum is correlated with possible rectal bleeding which occurs after treatment. It is therefore important not subject this possibly more sensitive area to excessive irradiation during radiotherapy treatment. Other areas and/or other organs are also concerned.

Given these constraints, precise knowledge is needed of the location of these areas to be avoided during treatment. Now, in most cases, these areas are not known and depend on individual characteristics, the shape of the rectum, its volume, the shape of the bladder, the patient's weight, etc. Thus, at present, for a specific patient, it is not possible to locate the sub-regions of the organs to be avoided during treatment with sufficient precision. In other words, there are no reports as yet of methods for using spatial information in prediction models and their inclusion in a radiotherapy planning step. There is huge anatomical and clinical variability which hinders the transfer of information from a population model to a specific patient.

In conclusion, there is existing equipment by these areas at risk can be avoided. This equipment offers better quality of care to patients but there are no methods for making efficient use of this equipment.

3. SUMMARY OF THE INVENTION

The proposed technique does not have these drawbacks of the prior art. More particularly, the proposed technique pertains to a method for producing data representing radiotherapy treatment constraints associated with a patient to be treated. Such a method comprises:
   a phase for matching at least one current atlas of a set of atlases as a function of at least one piece of data representing a patient to be treated, delivering a map of probability of regions at risk;
   a phase for generating at least one piece of data representing a constraint to be applied to a treatment intended for said patient as a function of said map of probability of regions at risk.

Thus, the proposed technique enables the regions at risk within the organs of the patient to be identified from pre-existing data which is processed and standardized to correspond to a given patient. Thus, the proposed method is used to identify sensitive areas within organs at risk, associated with a secondary effect. The invention thus enables the definition of spatial constraints in sub-regions in order to reduce the risk of toxicity in personalized planning context.

According to one particular embodiment, said method furthermore comprises a phase for planning at least one radiotherapy treatment as a function of said at least one piece of data representing a constraint (C).

According to one particular embodiment, said method furthermore comprises a phase for predicting toxicity for said patient as a function of said at least one piece of data representing said patient to be treated and of said at least one piece of data representing a constraint (C) generated.

According to one particular embodiment, said phase for matching at least one current atlas of said set of atlases comprises:
   a step of registration, through at least one determined registration parameter, of at least one part of said pieces of data of said current atlas ON said at least one piece of data representing said patient, delivering a registered current atlas containing raw probabilistic data;

a step of computation, by means of said at least one piece of data representing said patient, of said map of probability of regions at risk as a function of said raw probabilistic data.

According to one particular embodiment, said phase for matching said at least one current atlas of said set of atlases furthermore comprises:

a step for computing a similarity between said current atlas and said at least one piece of data representing said patient, delivering a value of similarity; and a step for weighting probabilistic data contained in said registered current atlas as a function of said value of similarity;

and said one step computing said map of probability of regions at risk by means of said at least one piece of data representing said patient is carried out as a function of the weighted probabilistic data.

According to one particular embodiment, said phase for generating at least one piece of data representing a constraint comprises:

a step for thresholding the map of probability of regions at risk as a function of a predetermined thresholding parameter;

a step for obtaining at least one 3D position of said area at risk for said patient, as a function of said thresholded map of probability of regions at risk;

a step for generating said at least one piece of data representing a constraint of treatment as a function of said position.

In another embodiment, the invention also relates to a device for producing data representing constraints of radiotherapy treatment associated with a patient to be treated. Such a device comprises:

means for matching at least one current atlas of said set of atlases as a function of said at least one piece of data representing a patient to be treated, delivering the map of probability of regions at risk;

means for generating at least one piece of data representing a constraint to be applied to a treatment intended for said patient as a function of said map of probability of regions at risk.

The described technique also pertains to a system for producing data representing constraints of radiotherapy treatment associated with a patient to be treated. Such a system comprises:

means for matching at least one current atlas of said set of atlases as a function of at least one piece of data representing a patient to be treated, delivering the map of probability of regions at risk;

means for generating at least one piece of data representing a constraint to be applied to a treatment intended for said patient as a function of said map of probability of regions at risk.

According to one preferred implementation, the different steps of the methods according to the invention are implemented by one or more software programs or computer programs comprising software instructions to be executed by a data processor of a relay module according to the invention and designed to control the execution of the different steps of the methods.

Consequently, the invention also pertains to a program capable of being executed by a computer or by a data processor, this program comprising instructions to control the execution of the steps of a method as mentioned here above.

This program can use any programming language whatsoever and can take the form of source code, object code or a code that is an intermediate code between source code and object code such as in a partially compiled form or in any other desirable form whatsoever.

The invention is also aimed at providing an information carrier readable by a data processor and comprising instructions of a program as mentioned here above.

The information carrier can be any entity or device whatsoever capable of storing the program. For example, the carrier can comprise a storage means such as a ROM, for example a CD-ROM or a microelectronic circuit ROM or again a magnetic recording means such as a floppy disk or a hard disk drive.

Furthermore, the information carrier can be a transmissible carrier such as an electrical or optical signal which can be conveyed via an electrical or optical cable by radio or by other means. The program according to the invention can be especially uploaded to an Internet type network.

As an alternative, the information carrier can be an integrated circuit into which the program is incorporated, the circuit being adapted to executing or being used in the execution of the method in question.

According to one embodiment, the invention is implemented by means of software and/or hardware components. In this respect, the term "module" may correspond in this document as much to a software component as to a hardware component or to a set of hardware and software components.

A software component corresponds to one or more computer programs, one or more sub-programs of a program or more generally to any element of a program or a piece of software capable of implementing a function or a set of functions as described here above for the module concerned. Such a software component is executed by a data processor of a physical entity (terminal, server, gateway, router, etc) and is capable of accessing hardware resources of this physical entity (memories, recording media, communications buses, input/output electronic boards, user interfaces, etc.).

In the same way, a hardware component corresponds to any element of a hardware unit capable of implementing a function or a set of functions as described here above for the module concerned. It can be a programmable hardware component or a component with an integrated processor for the execution of software, for example an integrated circuit, a smartcard, a memory card, an electronic board for the execution of firmware, etc.

Each component of the above-described system naturally implements its own software modules.

The different embodiments mentioned here above can be combined with one another to implement the invention.

4. FIGURES

Other features and advantages of the invention shall appear more clearly from the following description of a preferred embodiment given by way of a simple illustratory and non-exhaustive example and from the appended drawings, of which.

5. DESCRIPTION OF ONE EMBODIMENT

5.1. Reminder of the Principle of the Technique

The proposed technique relies on several distinct elements. In the first place, the technique relies on the creation of a set of data called a set of atlases. An atlas is a set of data representing certain characteristics. More specifically, an atlas comprises an image (a medical image, preferably in three dimensions, comprising pixels in three dimensions called voxels) with which several characteristics are associated. More particularly, an atlas integrates the locations and the shapes of the anatomical structures and the spatial relationships between these shapes and these structures.

In general, two categories of atlases can be distinguished. The first category is directly obtained from data of one patient only. This is an atlas associated with a patient. The second category is obtained from data corresponding to several patients. In this case, these are atlases comprising combined data, or averages, the purpose of which is to serve as a reference. One problem related to these prior-art atlases is that they correspond to a set of given organs. More particularly, in the case of data corresponding to cancer of the prostate, the atlases in question concern the entire prostate region which includes not only the prostate but also the rectum, the bladder, the urethra, etc. These atlases therefore do not relate to a specific element.

Since the object of the described technique is to prevent or to reduce side effects and since these side effects are attributed to excessively high doses of irradiation of one or more sensitive areas within organs and since these sensitive areas are in principle unknown for a given patient, another type of atlas needs to be used.

This novel type of atlas is of a combinational type comprising a 3D image derived from the combination of several original 3D images. These original 3D images either come from a same patient (in this case these original images can be obtained at different times) or come from several patients. In this atlas, therefore, combined anatomical data is available. This novel type of atlas has a specific feature of including not only combined anatomical data but also subsequently obtained clinical data. This subsequently obtained clinical data includes especially the occurrence of side effects. In cancer of the prostate, the side effects are for example rectal bleeding. In the case of head and throat cancer, it is the loss of taste or the absence of saliva. In this novel atlas, there is also a distribution of combined doses available. This distribution of doses of the atlas results from the computation made on the distributions of unit doses. These distributions of unit doses are those associated with unit images which have been used to produce the combined image included in the atlas. Depending on the clinical data (side effects) on the distribution of the doses, an atlas is produced from which a voxel-based analysis can be implemented to determine the dose received for a given voxel or for a given set of voxels and correlate this information with the occurrence of side effects. In the proposed technique, an atlas therefore relates to information associated with a probable area related to the side effects measured. Thus, through data from several patients in a population, an automatic method is used to build at least one atlas which defines sub-regions within the organs that are related to the dose and the toxicity.

The idea on which the proposed technique is based is to have several atlases of this type available. These atlases are grouped into a set of atlases. The atlases of this set of atlases are separated by at least one characteristic (at least one piece of clinical data and/or at least one piece of anatomical data). Given the availability of information on the side effects associated with the patients, for a current atlas of a set of atlases and according to the distribution of a combined doses, a probable location is available of an area that has contributed to the occurrence of the side effects to be avoided (these are pieces of probabilistic data of location of areas associated with said current atlas). What has just been explained is the principle of the proposed technique.

Figure 1:
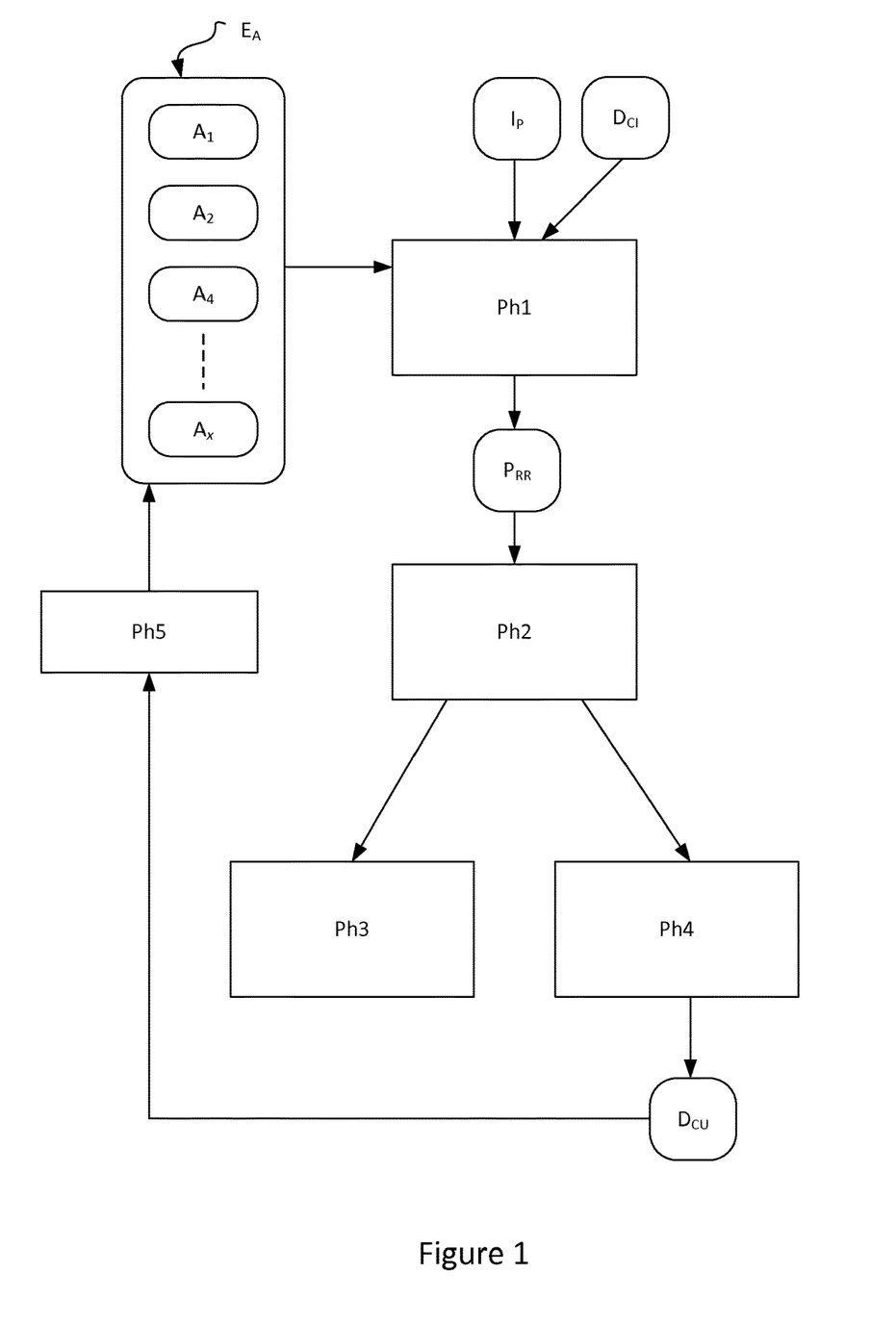
FIG. 1 is a block diagram of the proposed technique.

Referring to FIG. 1, we describe the different phases of the proposed technique. To begin with, there is a set of atlases ($E_{(A)}$) available, comprising x atlases ($A_1$ to $A_x$). This set of atlases is used in a first phase (Ph1), to be matched with a patient to be scheduled for whom firstly an image ($I_P$) and secondly initial clinical data ($D_{CI}$) are available. These pieces of initial clinical data pertain for example to age, weight, height, medical history and cancer pathology.

Thus, using the set of atlases ($E_{(A)}$) and at least one 3D image ($I_P$) corresponding to a patient to be planned for (and treated), at least one matching is made between the atlases of the set of atlases and the patient to be planned for. Thus, for a new patient to be planned for, the atlas or atlases are matched (spatially, clinically and temporally). Complementarily, when several atlases are successively matched with the basic image, these atlases can be weighted by taking account of the similarity between each atlas and the patient when the matching is made.

This matching phase makes it possible to obtain a map of probability of regions at risk ($P_{RR}$) for the patient to be scheduled. This map of probability makes it possible to situate the area or areas, on the patient to be scheduled, that will most probably be the source of the side effects for this patient. This map is a set of data comprising a probability that a given voxel will be situated in a region associated with greater radio-sensitivity. The second phase (Ph2) consists in generating constraints specific to the patient according to the map of probability of regions at risk ($P_{RR}$). These constraints specific to the patient can be generated automatically by the treatment console. The term "constraint" (C) denotes a data structure representing an area or a sub-region that is supposed to be sensitive to radiation. This structure of data can take several forms. A first form is that of a binary 3D image. This image comprises 0s in the voxels that do not form part of the area at risk and 1s in the voxels that form part of the area at risk. A second form is that of a probabilistic 3D image in which the voxels carry probabilistic information. Another form is a descriptive data structure identifying the coordinates of the area at risk in the coordinate space of the planning console.

With the areas inside the organs at risk being identified, the third phase (Ph3) consists in making a treatment schedule for the patient. This task is also implemented automatically by means of the treatment console. The constraints enable the console to schedule this patient's treatment for example by avoiding the sub-regions of the organs at risk or by reducing the planned dose on these same sub-regions. Depending on the form taken by the constraints, their integration into the planning console is modified.

The fourth phase (Ph4) which is carried out in parallel with the third phase implements a prediction of toxicity for the patient according to individual characteristics and new constraints generated with respect to treatment by IMRT, ARC and Cyber-Knife, which enable small regions to be targeted with precision. This planning is aimed at reducing the risks of toxicity related to the demarcated area. More particularly, this prediction phase comprises at least one step for assessing a dose received by said patient during said treatment, such as for example at least one step for computing a volume dose received within said area at risk as a function of the map of probability of regions at risk ($P_{RR}$) and at least one step for computing a probability of toxicity resulting from the application of a dose to said area at risk. This computation is iterated as many times as there are treatment sessions in order to obtain a probability of occurrence of side effects of the treatment. In a context of control of the tumor and reduction of toxicity, the proposed technique then provides a set of steps needed to personalize the treatment with a possible quantification of the benefit in terms of toxicity of the treatment.

Finally, the last phase (Ph5) consists of the reintroduction, anonymously, of the subsequent clinical data ($D_{CU}$) obtained at the end of the third phase, in the set of atlases ($E_{(A)}$). More particularly, from the introduction of these new pieces of data, it is possible to recompute a new set of atlases which take account especially of the side effects suffered by the patient who has just been treated.

5.2. Description of One Embodiment

In this embodiment, the previously described technique is applied to the treatment of cancer of the prostate. In a context of individualization of the intensity modulated radiotherapy treatment (IMRT), the technique presented in this embodiment generates a spatial constraint specific to a given patient in order to reduce the toxicity of the doses and/or predict the toxicity of the doses for organs or areas at risk. More particularly, an object of this technique in one particular application is to reduce rectal bleeding or even to eliminate its appearance.

In this embodiment, a set of atlases ($E_{(A)}$) is considered to be available. This set of atlases is built by a method for building atlases that is described here below. This set of atlases is built prior to the application of the present technique. According to a first variant, it is built immediately before the implementing of the present technique. According to a second variant, the set of atlases is built upstream, for example during a phase of installation or of parametrizing of a treatment device (a treatment console). According to a third variant, the atlas is available through a communications network and is for example pooled among the various apparatuses (different consoles) and the proposed technique is implemented on this communications network.

In this embodiment, the technique comprises:
  a phase (Ph1) for matching at least one current atlas ($A_i$) of said set of atlases ($E_{(A)}$) as a function of at least one piece of data representing a patient to be treated, delivering the map of probability of regions at risk ($P_{RR}$);
  a phase (Ph2) for generating at least one piece of data representing a constraint (C) to be applied to a treatment intended for said patient according to said map of probability of regions at risk ($P_{RR}$).

Figure 2:
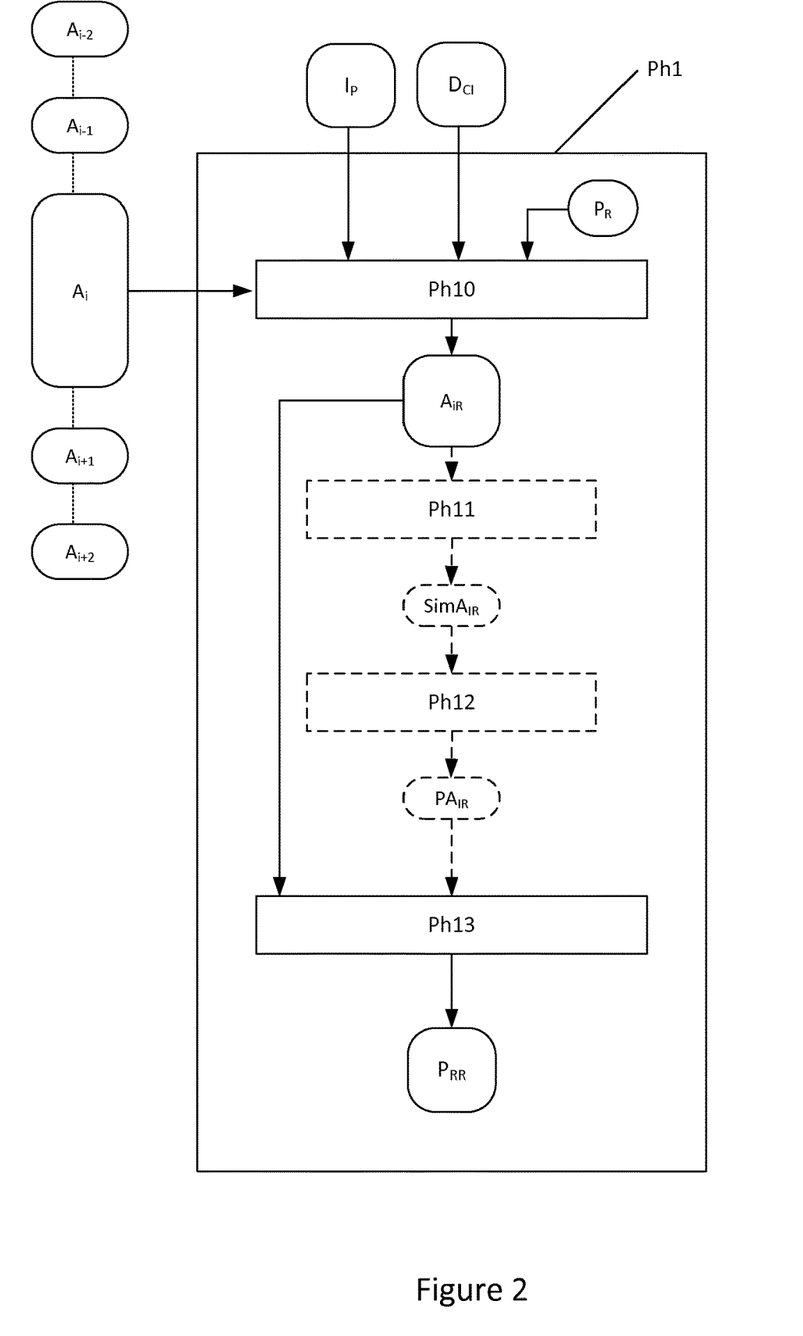
FIG. 2 illustrates the first phase of the proposed technique.

More particularly, with reference to FIG. 2, the phase (Ph1) for matching comprises, for said current atlas ($A_i$) of said set of atlases ($E_{(A)}$):
  a step (Ph10) for the registration, by said at least one determined registration parameter ($P_R$), of at least a part of said pieces of data of said current atlas ($A_i$) on said at least one piece of data representing said patient ($I_P$, $D_{Cl}$), delivering a registered current atlas ($A_{IR}$) containing raw probabilistic data;
  This phase (Ph1) for matching can be implemented for each atlas of said set of atlases ($E_{(A)}$).
  Depending on a configuration parameter, this phase also comprises:
  a step for computing a similarity (Ph11) between said registered current atlas ($A_{IR}$) and said at least one piece of data representing said patient ($I_P$, $D_{Cl}$), delivering a value of similarity ($SimA_{IR}$); and
  a step of weighting (Ph12) of probabilistic data contained in said registered current atlas ($A_{IR}$) as a function of said value of similarity delivering a value of weighting ($PA_{IR}$);

Besides, the phase for matching also comprises:
  a step of computation (Ph13), by means of said at least one piece of data representing said patient ($I_P$, $D_{Cl}$), of said map of probability of areas at risk ($P_{RR}$) as a function of either said raw probabilistic data or of weighted probabilistic data.

When the set of atlases comprises several atlases, the step of computation Ph13 is carried out by means of data of the atlases that have undergone a registration operation. Thus, the steps Ph10, Ph11 and Ph12 can be repeated as many times as there are atlases in the set of atlases ($E_{(A)}$) or on a subset of the atlases of the set of atlases ($E_{(A)}$). This is shown in the figure by the atlases $A_{I-2}$ to $A_{I+2}$. This means that Ph13 is either implemented step by step as a function of the results of the previous steps or directly by compiling the previously performed registration and the weighting operations in a single step.

Thus, at the end of this phase, probabilistic data ($P_{RR}$) is available and is, so to speak, aligned with the patient's data and more particularly the patient's anatomical data in the form of a 3D map of probability of regions at risk ($P_{RR}$). This map comprises, for each voxel, in addition to the usual data, a probability of a presence of an area at risk. The previous steps are implemented automatically, either by the treatment console itself or by means of a computation resource accessible through the communications network.

Figure 3:
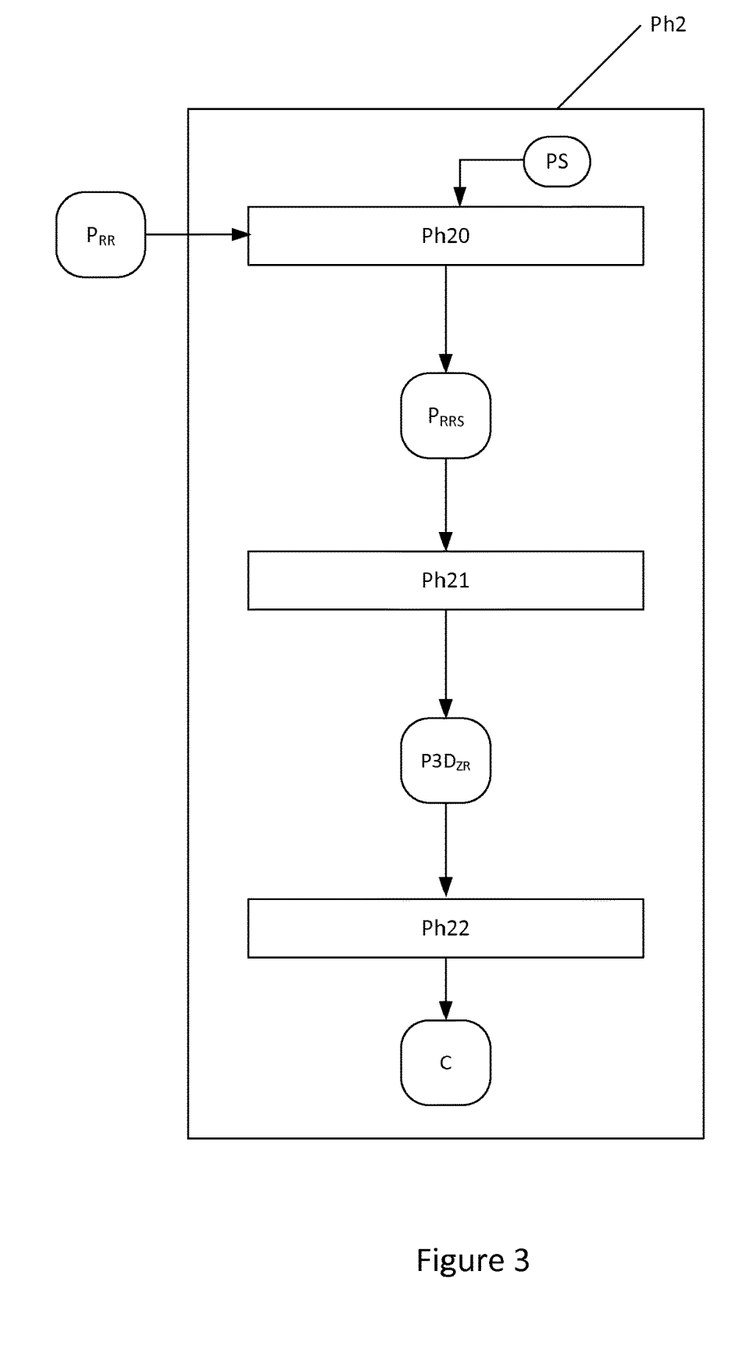
FIG. 3 illustrates the second phase of the proposed technique.

More particularly, the phase (Ph2) for generating at least one piece of data representing a constraint (C) comprises:
  a step (Ph20) for thresholding the map of probability of regions at risk ($P_{RR}$) as a function of a predetermined thresholding parameter (PS). In one specific embodiment, said thresholding parameter is equal to 0.5. We thus consider that any probability of sensitivity lower than 0.5 is equivalent to an absence of sensitivity and that any probability of a sensitivity greater than or equal to 0.5 is equivalent to a sensitivity.
  In one embodiment, this thresholding step is implemented on the map of probability of regions at risk ($P_{RR}$) independently, voxel by voxel. In another embodiment, this thresholding step is implemented on a set-wise basis, in considering for example that a low-probability voxel (probability below 0.5) that has a certain number of high-probability vowels (with a probability of over 0.5), for example more than 13 voxels, is an anachronism and is considered to be a voxel of high probability. In other words, the method comprises a step for thresholding probabilities of presence of a sensitive area according to a predetermined thresholding parameter, delivering at least one piece of data representing a presence of a sensitive area.
  a step (Ph21) for obtaining, as a function of said thresholded map of probability of regions at risk ($P_{RRS}$), at least on 3D position of said area at risk for said patient ($P3D_{ZR}$). Obtaining this position can be done either by transmission, using a communications network, of a position computed within the network or again by means of a computation made within the treatment console itself.
  In at least one particular embodiment, the area at risk is likened to an organ within said console. This makes it possible to circumvent an impossibility, for certain consoles, of identifying particular areas in certain organs. In other words, there is a step of integration, into a treatment-planning operation, of data representing a presence of a sensitive area.

a step (Ph22) for generating said at least one piece of data representing a constraint (C) of treatment as a function of said position (P3D$_{ZR}$).

Thus, at the end of this phase, there are constraints associated with the patient in the context of the treatment intended for him. These constraints can take the form of specific doses to be applied to the area or areas at risk identified. These constraints can also take the form of a set of spatial coordinates defined in the console and marked in a specific way for the radiotherapy treatment operator so that he himself determines the doses that will be applied.

5.3. Building the Set of Atlases

The set of atlases (E$_{(A)}$) is a multi-varied model of prediction of toxicity. It is a result of a local analysis (by voxel) of individual doses on a given population. In other words, unlike the usual atlases, the set of atlases (E$_{(A)}$) of the present technique comprises clinical data correlated with the doses scheduled or effectively received by the patients. These pieces of data are integrated into the atlas. Thus, this set of atlases is a multi-varied module (comprising several grades of toxicity, several reference spaces, several types of clinical variables) resulting from of an analysis of population. It makes it possible to set up relationships between distributions of doses in three dimensions, obtained during the scheduling or by measurement and the toxicity of these received doses. Several reference spaces (or atlases) are used depending on the inter-individual criteria of similarity.

Methods are known in the prior-art techniques for obtaining an atlas from a given population. Unlike these prior-art techniques, the technique described herein can be used to obtain several atlases from a given population. These different atlases can be obtained from one basic method. However, each of the different atlases corresponds to a pre-determined parameter. Indeed, in the prior art techniques, an atlas corresponds to a set of data corresponding to a synthesis of parameters. In the technique that is the object of the present application, an atlas corresponds to a synthesis oriented from only one initial parameter.

More specifically, the technique presented here comprises:

a phase of recognition and marking, by one or more expert methods, of the position of one or more sub-regions of the organs in the different images intended for the atlas; the experts used are automatic methods (based on population analyses).

a phase for determining a reference image from among the previous images;

a phase of application, as a function of a plurality of preliminarily known doses, of a distribution of doses on the marked images. This phase of application can be implemented by means of a deformation applied to the images as a function of the reference images;

a phase for standardizing the images as a function of a reference image;

a phase for determining a standardized distribution of doses by means of previous information.

Thus, there is a consistent distribution of doses applied to a particular patient.

5.4. Device for Implementing the Proposed Technique

Figure 4:
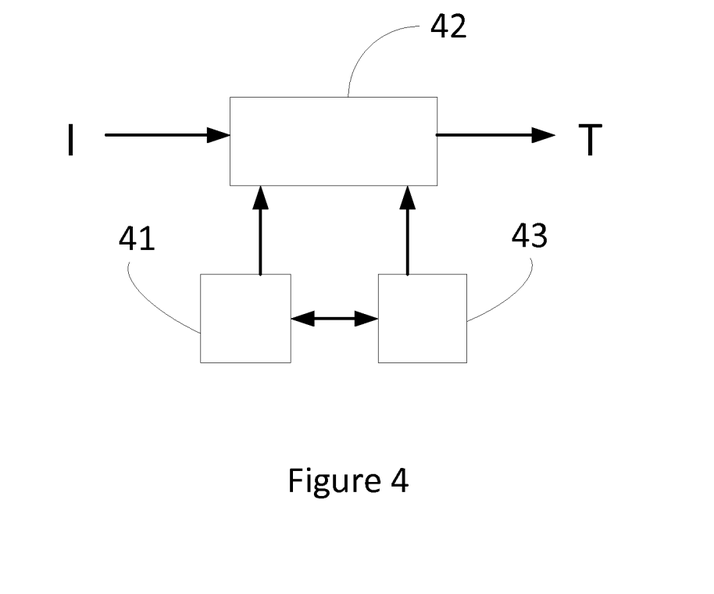
FIG. 4 describes a device for implementing the proposed technique.

Referring to FIG. 4, we present a simplified architecture of a device capable of implementing the described technique. Such a device comprises a memory 41, a processing unit 42 equipped for example with a microprocessor and driven by the computer program 43 implementing at least one part of the method as described. In at least one embodiment, the invention is implemented in the form of an application installed on a scheduling device. Such a device comprises:

means for matching at least one current atlas (A$_i$) of said set of atlases (E$_{(A)}$) as a function of at least one piece of data representing a patient to be treated delivering the map of probability of regions at risk (P$_{RR}$). These means can take the form of a connection interface (I) with one or more communications networks. They can be software interfaces or hardware interfaces (of the network board or network communications hardware module type). These means can take the form of dedicated computation resources used to carry out processing operations within the very device itself;

means (Ph2) for generating at least one piece of data representing a constraint (C) to be applied to a treatment intended for said patient according to said map of probability of regions at risk (P$_{RR}$);

means for transmitting (T) the previously generated data to a treatment device.

In at least one embodiment, the technique described can be implemented by means of a communications network to which a device is connected. In at least one embodiment, the technique described is implemented within a radiotherapy treatment planning console.

The invention claimed is:

1. A method for producing data representing radiotherapy treatment constraints associated with a patient to be treated, the method being implemented by an electronic apparatus, the method comprising:

the electronic apparatus matching at least one current atlas of a set of atlases as a function of at least one piece of data representing the patient to be treated, delivering a map of probability of sub-regions at risk, said map of probability comprising a set of data comprising a probability that a given voxel is situated in a sub-region associated with greater radio-sensitivity, delivering at least one generated constraint; and the electronic apparatus generating at least one piece of data representing a constraint of treatment to be applied to a treatment intended for said patient as a function of said map of probability of sub-regions at risk.

2. The method according to claim 1, wherein the method furthermore comprises the electronic apparatus planning at least one radiotherapy treatment as a function of said at least one piece of data representing a constraint.

3. The method according to claim 1, wherein the method furthermore comprises the electronic apparatus predicting toxicity for said patient as a function of said at least one generated constraint.

4. The method according to claim 1, wherein the matching at least one current atlas of said set of atlases comprises the electronic apparatus performing:

registration, through at least one determined registration parameter, of at least one part of pieces of data of said at least one current atlas on said at least one piece of data representing said patient, delivering a registered current atlas containing raw probabilistic data; and computation, by using said at least one piece of data representing said patient, of said map of probability of sub-regions at risk as a function of said raw probabilistic data.

5. The method according to claim 4, wherein the matching at least one current atlas of said set of atlases further comprises the electronic apparatus performing:

computing a similarity between said at least one current atlas and said at least one piece of data representing said patient, delivering a value of similarity; and weighting probabilistic data contained in said registered current atlas as a function of said value of similarity;

and said computing said map of probability of sub-regions at risk by using said at least one piece of data representing said patient is carried out as a function of the weighted probabilistic data.

6. The method according to claim 1, wherein the generating at least one piece of data representing a constraint comprises the electronic apparatus performing:

thresholding the map of probability of sub-regions at risk as a function of a predetermined thresholding parameter;

obtaining at least one 3D position of said sub-regions at risk for said patient, as a function of said thresholded map of probability of sub-regions at risk; and generating said at least one piece of data representing a constraint of treatment as a function of said at least one 3D position.

7. An electronic device comprising:

a processor; and a non-transitory computer-readable medium comprising instructions stored thereon, which when executed by the processor configure the electronic device to perform acts comprising:

producing data representing constraints of radiotherapy treatment associated with a patient to be treated, wherein the producing comprises:

matching at least one current atlas of a set of atlases as a function of at least one piece of data representing a patient to be treated, delivering a map of probability of sub-regions at risk, said map of probability comprising a set of data comprising a probability that a given voxel is situated in a sub-region associated with greater radio-sensitivity, delivering at least one generated constraint; and generating at least one piece of data representing a constraint to be applied to a treatment intended for said patient as a function of said map of probability of sub-regions at risk.

8. A system comprising:

a processor; and a non-transitory computer-readable medium comprising instructions stored thereon, which when executed by the processor configure the system to perform acts comprising:

producing data representing constraints of radiotherapy treatment associated with a patient to be treated, wherein the producing comprises:

matching at least one current atlas of a set of atlases as a function of at least one piece of data representing a patient to be treated, delivering a map of probability of sub-regions at risk, said map of probability comprising a set of data comprising a probability that a given voxel is situated in a sub-region associated with greater radio-sensitivity, delivering at least one generated constraint; and generating at least one piece of data representing a constraint to be applied to a treatment intended for said patient as a function of said map of probability of sub-regions at risk.

9. The system according to claim 8, wherein the system is further configured to produce a prediction of toxicity for said patient as a function of said at least one piece of data representing said patient to be treated and of said at least one generated constraint.

10. A non-transitory computer-readable medium comprising a computer program product stored thereon and executable by a microprocessor, wherein the program comprises program code instructions that when executed by the microprocessor configure the microprocessor to perform a method for producing data representing radiotherapy treatment constraints associated with a patient to be treated, the method comprising:

matching at least one current atlas of a set of atlases as a function of at least one piece of data representing the patient to be treated, delivering a map of probability of sub-regions at risk, said map of probability comprising a set of data comprising a probability that a given voxel is situated in a sub-region associated with greater radio-sensitivity, delivering at least one generated constraint; and generating at least one piece of data representing a constraint to be applied to a treatment intended for said patient as a function of said map of probability of sub-regions at risk.

* * * * *